United States Patent [19]

Thomas et al.

[11] Patent Number: 4,752,324
[45] Date of Patent: Jun. 21, 1988

[54] CERTAIN 2-(5-HYDROCARBYL OR ARYL-1-ALKYL-PYRAZOL-3-YL)-NICOTINIC ACID DERIVATIVES HAVING HERBICIDAL ACTIVITY

[75] Inventors: Rudolf Thomas; Peter Babczinski, both of Wuppertal; Hans-Joachim Santel; Ludwig Eue, both of Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 927,910

[22] Filed: Nov. 5, 1986

[30] Foreign Application Priority Data

Nov. 9, 1985 [DE] Fed. Rep. of Germany ....... 3539809
Jul. 11, 1986 [DE] Fed. Rep. of Germany ....... 3623302

[51] Int. Cl.$^4$ .................... C07D 401/04; A01N 43/56
[52] U.S. Cl. ............................................ 71/92; 71/94; 546/275; 546/276; 546/318; 544/33
[58] Field of Search ............................ 546/276; 71/92

[56] References Cited

FOREIGN PATENT DOCUMENTS 0041623 12/1981 European Pat. Off. ............ 546/281
2600655 7/1976 Fed. Rep. of Germany ...... 548/136

Primary Examiner—Alan L. Rotman

Attorney, Agent, or Firm—Sprung Horn Kramer & Woods

[57] ABSTRACT

Herbicidally active novel nicotinic acid derivatives of the formula

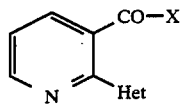

in which
X represents hydroxyl, alkoxy or the radical —OM,
wherein
M represents one equivalent of an alkali metal or alkaline earth metal ion, or an optionally substituted ammonium ion, and
Het represents isoxazolyl, pyrimidinyl or pyrazolyl each substituted by a substituent selected from the group consisting of alkyl, alkenyl, alkoxy, alkylthio, alkylamino, hydroxyl, mercapto, amino, alkylcarbonyl which is optionally substituted by halogen or alkoxy; cycloalkyl and in each case optionally substituted phenyl or naphthyl, or optionally substituted condensed cycloalkylpyrazolyl.

9 Claims, No Drawings

CERTAIN 2-(5-HYDROCARBYL OR ARYL-1-ALKYL-PYRAZOL-3-YL)-NICOTINIC ACID DERIVATIVES HAVING HERBICIDAL ACTIVITY

The invention relates to new nicotinic acid derivatives, several processes for their preparation and their use as herbicides.

It is already known that certain hetero-substituted benzoic acid derivatives have plant growth-regulating properties and that certain imidazoline-nicotinic acid derivatives have herbicidal properties (compare DE-OS (German Published Specification) No. 2,600,655 and European Patent A-41,623). However, their action is not always completely satisfactory in all fields of use.

New nicotinic acid derivatives of the general formula (I)

$$\text{(I)}$$

in which
X represents hydroxyl, alkoxy or the radical —OM, wherein
  M represents one equivalent of an alkali metal or alkaline earth metal ion, or an optionally substituted ammonium ion, and
  Het represents in each case substituted isoxazolyl, pyrimidinyl or pyrazolyl, possible substituents in each case being alkyl, alkenyl, alkoxy, alkylthio, alkylamino, hydroxyl, mercapto, amino, alkylcarbonyl which is optionally substituted by halogen or alkoxy, cycloalkyl and in each case optionally substituted phenyl or naphthyl, furthermore pyrazolyl may contain a condensed cycloalkyl part which is optionally substituted,
have been found.

It has furthermore been found that the new nicotinic acid derivatives of the formula (I)

$$\text{(I)}$$

in which
X represents hydroxyl, alkoxy or the radical —OM, wherein
  M represents one equivalent of an alkali metal or alkaline earth metal ion, or an optionally substituted ammonium ion, and
  Het represents in each case substituted isoxazolyl, pyrimidinyl or pyrazolyl, possible substituents in each case being alkyl, alkenyl, alkoxy, alkylthio, alkylamino, hydroxyl, mercapto, amino, alkylcarbonyl which is optionally substituted by halogen or alkoxy, cycloalkyl and in each case optionally substituted phenyl or naphthyl, furthermore pyrazolyl may contain a condensed cycloalkyl part which is optionally substituted,
are obtained by a process in which
(A) diketones of the formula (II)

$$\text{(II)}$$

in which
$X^1$ represents alkoxy and
$R^1$ represents alkyl, alkenyl, cycloalkyl or acetyl, or represents optionally substituted phenyl or naphthyl,
are reacted
(a) with hydroxylamine or salts thereof to give the nicotinic acid derivatives of the formula (Ia)

$$\text{(Ia)}$$

in which
$X^2$ represents hydroxyl or alkoxy and
$Het^1$ represents substituted isoxazolyl, possible substituents being alkyl, alkenyl, cycloalkyl, acetyl and in each case optionally substituted phenyl or naphthyl, or (b) with amidines of the general formula (III) or salts thereof $$R^2-\underset{\underset{NH_2}{|}}{C}=NH \qquad \text{(III)}$$

in which
$R^2$ represents alkyl, alkoxy, alkylthio, alkylamino or optionally substituted phenyl,
to give the nicotinic acid derivatives of the formula (Ib)

$$\text{(Ib)}$$

in which
$X^2$ has the abovementioned meaning and
$Het^2$ represents substituted pyrimidinyl, possible substituents being alkyl, alkenyl, cycloalkyl, alkoxy, alkylthio, alkylamino, acetyl and in each case optionally substituted phenyl or naphthyl, or (c) with urea derivatives of the general formula (IV), or salts thereof $$NH_2-\underset{\underset{}{\overset{\overset{Y}{||}}{C}}}{}-NH_2 \qquad \text{(IV)}$$

in which
Y represents oxygen, sulphur or the radical NH, to give the nicotinic acid derivatives of the formula (Ic)

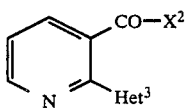 (Ic)

in which
X² has the abovementioned meaning and
Het³ represents substituted pyrimidinyl, possible substituents being alkyl, alkenyl, cycloalkyl, hydroxyl, mercapto, amino, acetyl and in each case optionally substituted phenyl or naphthyl, in the presence of a diluent,
or in that (B) if appropriate, the nicotinic acid derivatives obtained by process (A), of the formula (Ie)

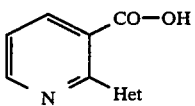 (Ie)

in which
Het has the abovementioned meaning,
are reacted with a base in the presence of a solvent in the customary manner to give the nicotinic acid derivatives of the formula (If)

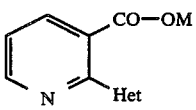 (If)

in which
M and Het have the abovementioned meanings, and
(C) 1,3-diketones of the formula (II)

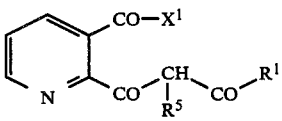 (II)

in which
X¹ represents alkoxy and
R¹ represents alkyl, alkenyl, cycloalkyl, acetyl, and in each case optionally substituted phenyl or naphthyl and
R⁵ represents hydrogen or
R¹ and R⁵ together represent an optionally substituted alkylene chain,
are reacted with hydrazines of the general formula (V)

 R⁴—NH—NH₂ (V)

in which
R⁴ represents hydrogen, alkyl, optionally by halogen or alkoxy substituted alkylcarbonyl or optionally substituted phenyl,
to give the nicotinic acid derivatives of the formula (Id)

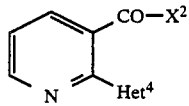 (Id)

in which
X² has the abovementioned meaning and
Het⁴ represents substituted pyrazolyl, possible substituents being alkyl, alkenyl, cycloalkyl, optionally by halogen or alkoxy substituted alkylcarbonyl and in each case optionally substituted phenyl or naphthyl, furthermore pyrazolyl may contain a condensed cycloalkyl part which is optionally substituted,
in the presence of a diluent.

Finally, it has been found that the new nicotinic acid derivatives of the general formula (I) have herbicidal properties.

Formula (I) provides a general definition of the nicotinic acid derivatives according to the invention. Preferred compounds of the formula (I) are those in which
X represents hydroxyl, or represents alkoxy with 1 to 6 carbon atoms, or represents the radical —OM,
wherein
M represents a sodium or potassium ion, or represents one equivalent of a magnesium or calcium ion, or represents an ammonium or mono-, di-, tri- or tetraalkylammonium ion with in each case 1 to 4 carbon atoms in the individual alkyl radicals and
Het represents

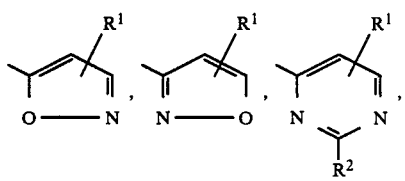

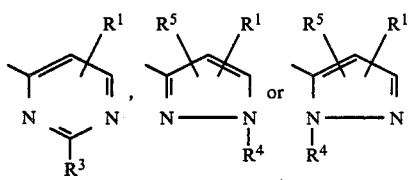

wherein
R¹ represents straight-chain or branched alkyl with 1 to 6 carbon atoms, or represents alkenyl with 2 to 6 carbon atoms, or represents cycloalkyl with 3 to 6 carbon atoms, or represents acetyl, or represents phenyl or naphthyl, in each case optionally mono-, di- or trisubstituted by identical or different substituents, possible substituents being: halogen, in each case straight-chain or branched alkyl, alkoxy, alkylthio and dialkylamino with 1 to 4 carbon atoms in the individual alkyl parts, halogenoalkyl with 1 or 2 carbon atoms and 1 to 5 identical or different halogen atoms, such as fluorine and chlorine atoms, nitro and phenyl,
R² represents in each case straight-chain or branched alkyl, alkoxy, alkylthio or alkylamino with 1 to 6 carbon atoms, or represents phenyl which is optionally mono-, di- or trisubstituted by identical or different substituents, possible substituents being halogen, straight-chain or branched alkyl and alkoxy with in each case 1 to 4 carbon atoms and halogenoalkyl with 1 or 2 carbon atoms and 1 to 5 identical or different halogen atoms, such as fluorine and chlorine atoms, $R^3$ represents hydroxyl or mercapto, or represents amino and $R^4$ represents hydrogen, or represents straight-chain or branched alkyl with 1 to 6 carbon atoms, or represents optionally by fluorine, chlorine and/or bromine or $C_1$–$C_4$-alkoxy substituted $C_1$–$C_4$-alkylcarbonyl, or represents phenyl which is optionally mono-, di- or trisubstituted by identical or different substituents, possible substituents being halogen, straight-chain or branched alkyl and alkoxy with in each case 1 to 4 carbon atoms and halogenalkyl with 1 or 2 carbon atoms and 1 to 5 identical or different halogen atoms, such as fluorine and chlorine atoms, $R^5$ represents hydrogen or $R^1$ and $R^5$ represent together an optionally benzannellated alkylene chain with 3 to 5 carbon atoms.

Particularly preferred compounds of the formula (I) are those in which

X represents hydroxyl, methoxy, ethoxy or n- or i-propoxy, or represents the radical —OM, wherein M represents the sodium, potassium or ammonium ion or a tetraalkylammonium ion with 1 to 4 carbon atoms in the individual alkyl radicals, and Het represents

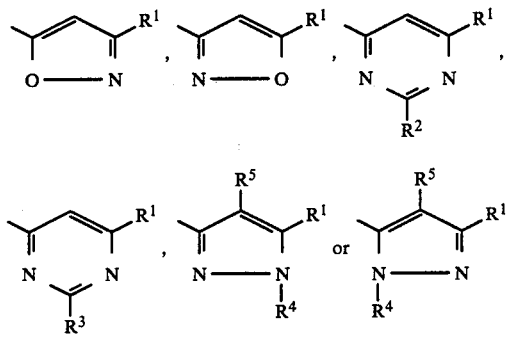

wherein $R^1$ represents methyl, ethyl, n- or i-propyl or n-, i-, s- or t-butyl, or represents vinyl or isopropylidene, or represents cyclopropyl, cyclopentyl, cyclohexyl or acetyl, or represents phenyl or naphthyl, in each case optionally mono- or disubstituted by identical or different substituents, possible substituents being: fluorine, chlorine, bromine, iodine, methyl, ethyl, n- and i-propyl, methoxy, ethoxy, n- and i-propoxy, methylthio, ethylthio, n- and i-propylthio, dimethylamino, diethylamino, dipropylamino, trifluoromethyl, nitro and phenyl, $R^2$ represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino or n- and i-propylamino, or represents phenyl which is optionally mono- or disubstituted by identical or different substituents, possible substituents being: fluorine, chlorine, bromine, methyl, ethyl, n- and i-propyl, methoxy, ethoxy, n- and i-propoxy and trifluoromethyl, $R^3$ represents hydroxyl, mercapto or amino and $R^4$ represents hydrogen, methyl, ethyl, n- or i-propyl, n-, i-, s- or t-butyl, acetyl, chloromethylcarbonyl, chloroethylcarbonyl, methoxymethylcarbonyl, ethoxymethylcarbonyl, methoxyethylcarbonyl, ethoxyethylcarbonyl,, or represents phenyl which is optionally mono- or disubstituted by identical or different substituents, possible substituents being; fluorine, chlorine, bromine, methyl, ethyl, n- and i-propyl, methoxy, ethoxy, n- and i-propoxy and trifluoromethyl, $R^5$ represents hydrogen or $R^1$ and $R^5$ represent together an optionally benzannelated alkylene chain with 3 or 4 carbon atoms.

An especially preferred group of compounds of the formula (I) here is that in which X represents hydroxyl, methoxy, ethoxy or n- or i-propoxy, or represents the radical —OM, wherein M represents a sodium potassium or ammonium ion or a tetraalkylammonium ion with 1 to 4 carbon atoms in the individual alkyl radicals, and Het represents

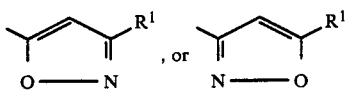

wherein $R^1$ represents methyl, ethyl, n- or i-propyl or n-, i-, s- or t-butyl, or represents vinyl or isopropylidene, or represents cyclopropyl, cyclopentyl, cyclohexyl or acetyl, or represents phenyl or naphthyl, in each case optionally mono- or disubstituted by identical or different substituents, possible substituents being: fluorine, chlorine, bromine, iodine, methyl, ethyl, n- and i-propyl, methoxy, ethoxy, n- and i-propoxy, methylthio, ethylthio, n- and i-propylthio, dimethylamino, diethylamino, dipropylamino, trifluoromethyl, nitro and phenyl.

Another especially preferred group of compounds of the formula (I) is that in which X represents hydroxyl, methoxy, ethoxy or n- or i-propoxy, or represents the radical —OM, wherein M represents the sodium, potassium or ammonium ion or a tetraalkylammonium ion with 1 to 4 carbon atoms in the individual alkyl radicals, and Het represents

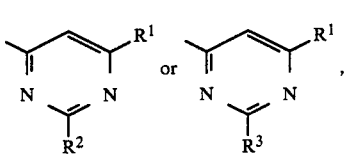

wherein $R^1$ represents methyl, ethyl, n- or i-propyl or n-, i-, s- or t-butyl, or represents vinyl or isopropylidene, or represents cyclopropyl, cyclopentyl, cyclohexyl or acetyl, or represents phenyl or naphthyl, in each case optionally mono- or disubstituted by identical or different substituents, possible substituents being: fluorine, chlorine, bromine, iodine, methyl, ethyl, n- and i-propyl, methoxy, ethoxy, n- and i-propoxy, methylthio, ethylthio, n- and i-propylthio, dimethylamino, diethylamino, dipropylamino, trifluoromethyl, nitro and phenyl, $R^2$ represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino or n- and i-propylamino, or represents phenyl which is optionally mono- or disubstituted by identical or different substituents, possible substituents being: fluorine, chlorine, bromine, methyl, ethyl, n- and i-propyl, methoxy, ethoxy, n- and i-propoxy and trifluoromethyl, and $R^3$ represents hydroxyl, mercapto or amino.

Another especially preferred group of compounds of the formula (I) is that in which X represents hydroxyl, methoxy, ethoxy or n- or i-propoxy, or represents the radical —OM, wherein M represents the sodium, potassium or ammonium ion or a tetraalkylammonium ion with 1 to 4 carbon atoms in the individual alkyl radicals, and Het represents

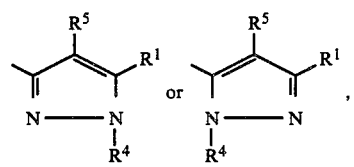

wherein $R^1$ represents methyl, ethyl, n- or i-propyl or n-, i-, s- or t-butyl, or represents vinyl or isopropylidene, or represents cyclopropyl, cyclopentyl, cyclohexyl or acetyl, or represents phenyl or naphthyl, in each case optionally mono- or disubstituted by identical or different substituents, possible substituents being: fluorine, chlorine, bromine, iodine, methyl, ethyl, n- and i-propyl, methoxy, ethoxy, n- and i-propoxy, methylthio, ethylthio, n- and i-propylthio, dimethylamino, diethylamino, dipropylamino, trifluoromethyl, nitro and phenyl and $R^4$ represents hydrogen, methyl, ethyl, n- or i-propyl or n-, i-, s- or t-butyl, acetyl, chloromethylcarbonyl, methoxymethylcarbonyl, or represents phenyl which is optionally mono- or disubstituted by identical or different substituents, possible substituents being: fluorine, chlorine, bromine, methyl, ethyl, n- and i-propyl, methoxy, ethoxy, n- and i-propoxy and trifluoromethyl, $R^5$ represents hydrogen or $R^1$ and $R^5$ together represent an optionally benzannelated alkylene chain with 3 or 4 carbon atoms.

If, for example, 2-(1,3-dioxo-3-t-butyl-prop-1-yl)-3-methoxycarbonyl-pyridine and hydroxylamine hydrochloride are used as starting substances, the course of the reaction in process (A-a) according to the invention can be represented by the following equation:

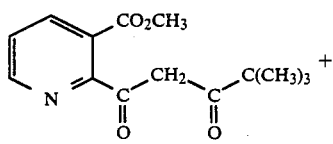

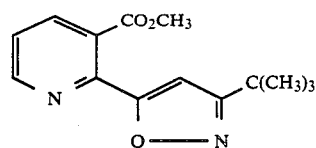

If, for example, 2-(1,3-dioxo-3-phenyl-prop-1-yl)-3-methoxycarbonyl-pyridine and isobutyrylamidine hydrochloride are used as starting substances, the course of the reaction in process (A-b) according to the invention can be represented by the following equation:

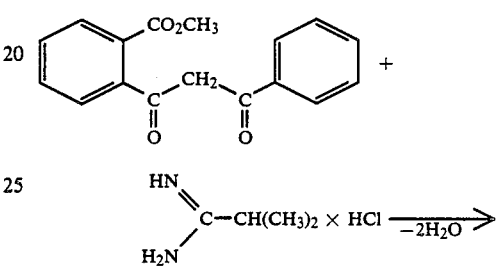

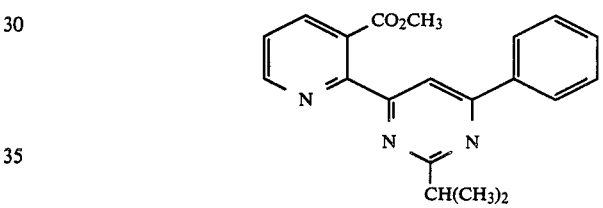

If, for example, 2-(1,3-dioxo-3-phenyl-prop-1-yl)-3-methoxycarbonylpyridine and urea are used as starting substances, the course of the reaction in process (A-c) according to the invention can be represented by the following equation:

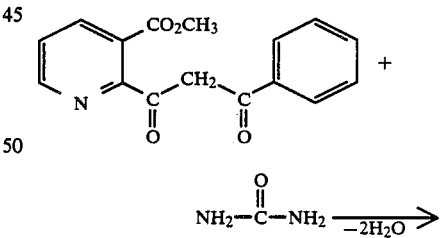

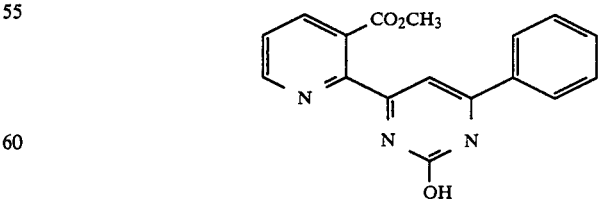

If, for example, 2-(5-isopropyl-pyrazol-3-yl)pyridine-3-carboxylic acid and calcium carbonate are used as starting substances, the course of the reaction in process (B) according to the invention can be represented by the following equation:

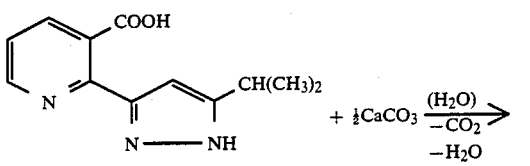

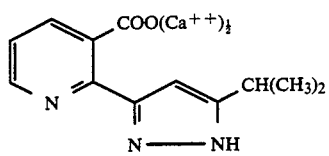

If, for example, 2-(1,3-dioxo-3-(4-methoxyphenyl)-prop-1-yl)-3-methoxycarbonyl-pyridine and methylhydrazine are used as starting substances, the course of the reaction in process (C) according to the invention can be represented by the following equation:

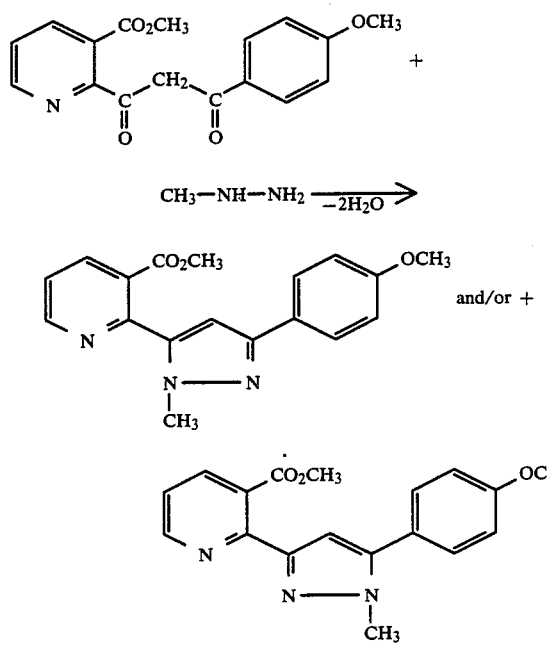

Formulae (II) and (IIa) provide a general definition of the diketones required as starting substances for carrying out processes (A) and (C) according to the invention. In the formulae (II) and (IIa), $R^1$ and $R^5$ preferably represent those radicals which have already been mentioned as preferred for these substituents in connection with the description of the substances of the formula (I) according to the invention, and $X^1$ preferably represents alkoxy with 1 to 6 carbon atoms, and particularly preferably represents methoxy, ethoxy and n- or i-propoxy.

The diketones of the formulae (II) and (IIa) and their corresponding enol forms are not yet known; however, they can be obtained in a generally known manner, by a process in which, for example, ketones of the formula (VI)

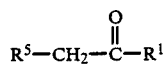   (VI)

in which $R^1$ and $R^5$ have the abovementioned meaning, are reacted with 2,3-dialkoxycarbonyl-pyridines of the formula (VII)

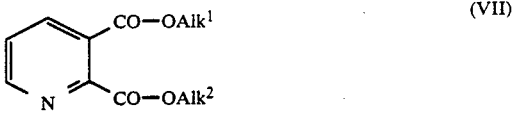   (VII)

in which

Alk$^1$ and Alk$^2$ can be identical or different and represent alkyl, preferably alkyl with 1 to 6 carbon atoms and particularly preferably methyl, ethyl and n- or i-propyl, in the presence of a strong base, such as, for example, sodium hydride, sodium amide or sodium alcoholates, such as sodium methylate or sodium ethylate, and in the presence of an inert organic solvent, such as, for example, toluene, xylene, dichlorobenzene or cyclohexane, at temperatures between 80° C. and 150° C.

The ketones of the formula (VI) and the 2,3-dialkoxycarbonyl-pyridines of the formula (VII) are generally known compounds of organic chemistry.

Formula (III), (IV) or (V) provides a general definition of the amidines, urea derivatives for carrying out processes (A) and (C) according to the invention. In formula (III) or (V), $R^2$ or $R^4$ preferably represents the radical which has already been mentioned as preferred for these substituents in connection with the description of the substances of the formula (I) according to the invention. In formula (IV), Y preferably represents oxygen, sulphur or the radical NH.

The hydroxylamine and the amidines of the formula (III) and the urea derivatives of the formula (IV) are preferably employed in the form of their salts, such as, for example, as hydrohalides or hydrosulphates.

Hydroxylamine and salts thereof, amidines of the formula (III) and salts thereof, urea derivatives of the formula (IV) and salts thereof and hydrazines of the formula (V) are generally known compounds of organic chemistry.

Inert, water-immiscible solvents, such as, for example, aromatic hydrocarbons, such as, in particular, toluene or benzene, chlorohydrocarbons, such as, in particular, carbon tetrachloride, or water-binding solvents, such as, in particular, a mixture of glacial acetic acid and sodium acetate, are possible, diluents for carrying out processes (A) and (C) according to the invention.

If the mixture of glacial acetic acid and sodium acetate is used, the ester radical in the 3-position is retained on heating for a short time, while the free acid is preferentially formed on prolonged heating.

The reaction temperatures can be varied within a substantial range in carrying out processes (A) and (C) according to the invention. The reaction is in general carried out at temperatures between 0° C. and 140° C., preferably at temperatures between 20° C. and 120° C.

For carrying out processes (A) and (C) according to the invention, the starting substances required are in general employed in approximately equimolar proportions. However, it is also possible to use one of the two components employed in each case in excess.

Working up is carried out by customary methods in processes (A) and (C) according to the invention.

The nicotinic acid derivatives of the formula (Ie) to be used as starting substances for carrying out process (B) according to the invention are compounds according to the invention and can be prepared by process (A).

Possible bases for process (B) according to the invention are all the alkali metal, alkaline earth metal and ammonium salts and mono-, di- and trialkylamines which can usually be employed. These include, preferably, potassium carbonate, sodium carbonate, calcium carbonate, magnesium carbonate, ammonium carbonate, diethylamine and triethylamine.

Possible solvents for reaction (B) according to the invention are, preferably, water-miscible organic solvents. These include, preferably, alcohols, such as methanol, ethanol and propanol, and ethers, such as tetrahydrofuran.

The reaction temperatures can be varied within a substantial range in carrying out process (B) according to the invention. The reaction is in general carried out at temperatures between $-30°$ C. and $100°$ C., preferably between $0°$ C. and $60°$ C.

The reaction in process (B) according to the invention is carried out in the customary manner, by a procedure in which solutions of the reaction partners in equimolar amounts are mixed and the salts which thereby precipitate are isolated by filtration or, if no precipitation occurs, by evaporation of the solution, and, if appropriate, are purified by recrystallization.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Braschiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention moreover also show fungicidal activity, such as, in particular, against Oomycetes and Pyricularia oryzae on rice, when applied in appropriate amounts and when in appropriate concentrations.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in their formulations, can also be used, for combating weeds, as mixtures with known herbicides, finished formulations or tank mixes being possible.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

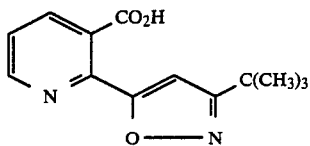

(I-1)

(Process A-a)

7.9 g (0.06 mole) of 2-(1,3-dioxo-3-t-butyl-prop-1-yl)-3-methoxycarbonylpyridine, 4.1 g (0.06 mole) of hydroxylamine hydrochloride and 6 g of sodium acetate are heated under reflux in 120 ml of glacial acetic acid for 3 hours. The reaction mixture is then poured into 1 l of water and extracted several times with a total of 300 ml of ethyl acetate. After the organic phase has been dried over sodium sulphate, it is evaporated in vacuo. The residue is extracted by boiling in portions of a total of 100 ml of water, the aqueous extracts are cooled to 10° C. and the colorless crystals which precipitate out are filtered off with suction and dried in vacuo.

4.2 g (57% of theory) of 2-(3-t-butyl-isoxazol-5-yl)-3-carboxylic acid pyridine are obtained as colorless crystals of melting point 113° C.

EXAMPLE 2

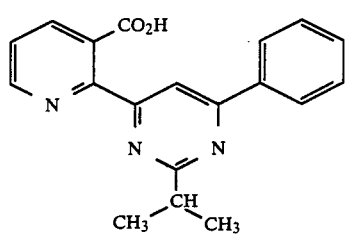

(I-2)

(Process A-b)

14.2 g (0.05 mole) of 2-(1,3-dioxo-3-phenyl-prop-1-yl)-3-methoxycarbonyl-pyridine, 12.3 g (0.1 mole) of isobutyrylamidine hydrochloride and 10 g of sodium acetate are heated under reflux in 200 ml of glacial acetic acid for 3 hours. The reaction mixture is then stirred into 1.5 l of water and extracted several times with a total of 2 l of ethyl acetate and the extracts are dried over sodium sulphate and evaporated in vacuo. The residue is chromatographed over silica gel with chloroform/ethyl acetate (V/V=1:1).

0.9 g (6% of theory) of 2-(2-isopropyl-6-phenyl-pyrimidin-4-yl)-3-carboxylic acid pyridine is obtained as colorless crystals of melting point 176° C. (decomposition).

Preparation of the starting substance:

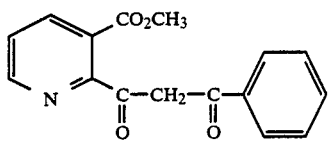

(II-1)

A solution of 19.5 g (0.1 mole) of 2,3-dimethoxycarbonyl-pyridine and 12 g (0.1 mole) of acetophenone in 300 ml of toluene is added dropwise to a suspension of 2.4 g (0.1 mole) of sodium hydride in 100 ml of toluene, while stirring. The mixture is then boiled under reflux for 3 hours, during which the methyl alcohol formed and about half of the toluene are distilled off. The residue which remains is poured onto a mixture of 15 g of ice and 7.2 g of acetic acid. The organic phase is separated off, the aqueous phase is extracted with chloroform (3 portions of 100 ml each) and the organic phases are combined, dried over sodium sulphate and evaporated in vacuo. The residue is fractionated over silica gel with chloroform as the mobile phase and chromatographed and the corresponding fractions are recrystalized from legroin.

17 g (60% of theory) of 2-(1,3-dioxo-3-phenyl-prop-1-yl)-3-methoxycarbonyl-pyridine are obtained as white crystals of melting point 87° C.

EXAMPLE 3

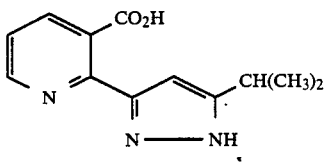

(I-3)

(Process C)

4 g (0.08 mole) of hydrazine hydrate are added dropwise to a solution of 10 g (0.04 mole) of 2-(1,3-dioxo-3-isoprop-1-yl)-3-methoxycarbonyl-pyridine in 150 ml of toluene. When the exothermic reaction has subsided, the mixture is subsequently stirred at 20° C. for 3 hours. The precipitate which has separated out is filtered off with suction and then stirred several times with water. The aqueous extracts are evaporated in vacuo.

6.6 g (71% of theory) of 2-(5-isopropyl-pyrazol-3-yl)-3-carboxylic acid pyridine are obtained as pale yellow crystals of melting point 203° C. (decomposition).

EXAMPLE 4 AND 5

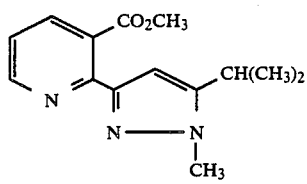
(I-4)

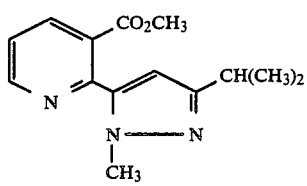
(I-5)

(Process C)

5.3 ml (0.1 mole) of methylhydrazine are added dropwise to 12.5 g (0.05 mole) of 2-(1,3-dioxo-3-isoprop-1-yl)-3-methoxycarbonyl-pyridine and 10 g of sodium acetate in 100 ml of glacial acetic acid, the reaction mixture being kept below 30° C. The reaction mixture is then subsequently stirred under reflux for 1 hour. It is poured onto 600 ml of water and extracted with ethyl acetate. The extract is washed neutral with sodium bicarbonate solution, dried over sodium sulphate and concentrated in vacuo.

12.5 g (96% of theory) of an oil which consists to the extent of 85.5% of 2-(5-isopropyl-1-methyl-pyrazol-3-yl)-3-methoxycarbonyl-pyridine and to the extent of 14.5% of 2-(5-isopropyl-2-methyl-pyrazol-3-yl)-3-methoxycarbonyl-pyridine are obtained.

The following compounds of the general formula (I)

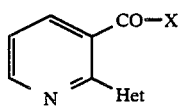
(I)

are obtained in an analogous manner by a process corresponding to the processes according to the invention:

TABLE 1

| Example No. | X | Het | Physical data |
|---|---|---|---|
| I-6 | OCH₃ | (structure with C(CH₃)₃, N—N—CH₃) | oil |
| I-7 | OCH₃ | (structure with C(CH₃)₃, CH₃—N—N) | oil |
| I-8 | OCH₃ | (structure with C(CH₃)₃, N—N-phenyl) | oil |
| I-9 | OCH₃ | (structure with C(CH₃)₃, phenyl-N—N) | oil |
| I-10 | OCH₃ | (structure with OCH₃-phenyl, CH₃—N—N) | Melting point: 160° C. |
| I-11 | OCH₃ | (structure with OCH₃-phenyl, N—N-CH₃) | Melting point: 160° C. |
| I-12 | OH | (structure with C(CH₃)₃, N—NH) | Melting point: 197° C. |
| I-13 | OH | (structure with OCH₃-phenyl, N—N-CH₃) | Melting point: 194° C.* |
| I-14 | OH | (structure with OCH₃-phenyl, N—NH) | Melting point: 148° C.* |
| I-15 | OH | (structure with CH(CH₃)₂, O—N) | Melting point: 123° C. |
| I-16 | OH | (structure with OCH₃-phenyl, O—N) | Melting point: 203° C.* |

TABLE 1-continued

| Example No. | X | Het | Physical data |
|---|---|---|---|
| I-17 | OH | (3-phenyl-isoxazol-5-yl methylidene group) | Melting point: 211° C. |
| I-18 | OH | (4-(4-methoxyphenyl)-2-isopropyl-pyrimidin-5-yl methylidene) | Melting point: 155° C. |
| I-19 | OH | (4-(4-methoxyphenyl)-2-phenyl-pyrimidin-5-yl methylidene) | Melting point: 200° C.* |
| I-20 | OH | (3-phenyl-1H-pyrazol-4-yl methylidene) | Melting point: 205° C.* |
| I-21 | OCH₃ | (3-(4-methoxyphenyl)-1H-pyrazol-4-yl methylidene) | Melting point: 110° C. |
| I-22 | OCH₃ | (3-phenyl-1H-pyrazol-4-yl methylidene) | Melting point: 95° C. |
| I-23 | OCH₃ | (3-isopropyl-1H-pyrazol-4-yl) | Oil |
| I-24 | OH | (3-phenyl-1-methyl-pyrazol-4-yl methylidene) | Melting point: 140° C. |
| I-25 | OCH₃ | (3-phenyl-1-methyl-pyrazol-4-yl methylidene) | Oil |
| I-26 | OCH₃ | (1-methyl-pyrazol-4-yl methylidene with phenyl) | Oil |
| I-27 | OH | (3-isopropyl-1-methyl-pyrazol-4-yl) | Melting point: 147° C. |
| I-28 | OH | (3-tert-butyl-1-methyl-pyrazol-4-yl) | Melting point: 203° C. |
| I-29 | OH | (3-isopropyl-1-phenyl-pyrazol-4-yl) | Melting point: 168° C. |
| I-30 | OCH₃ | (3-isopropyl-1-phenyl-pyrazol-4-yl) | Oil |
| I-31 | OCH₃ | (5-isopropyl-2-phenyl-pyrazol-3-yl) | Oil |
| I-32 | OH | (5-tert-butyl-2-phenyl-pyrazol-3-yl) | Melting point: 115° C. |
| I-33 | OCH₃ | (3-(4-chlorophenyl)-1-methyl-pyrazol-4-yl methylidene) | Melting point: 145° C. |

TABLE 1-continued

| Example No. | X | Het | Physical data |
|---|---|---|---|
| I-34 | OCH$_3$ | (methyl group)-C(=N-N(CH$_3$)-)-CH=C(-4-Cl-C$_6$H$_4$) | Melting point: 145° C. |
| I-35 | OCH$_3$ | (methyl)-C(=N-NH-)-CH=C(-4-Cl-C$_6$H$_4$) | Melting point: 167° C. |
| I-36 | OCH$_3$ | (methyl)-C(=N-NH-)-CH=C(2-naphthyl) | Melting point: 185° C. |
| I-37 | OCH$_3$ | (methyl)-C(=N-N(CH$_3$)-)-CH=C(2-naphthyl) | Melting point: 116° C. |
| I-38 | OH | (methyl)-C(=N-O-)-CH=C(4-biphenyl) | Melting point: 206° C.* |
| I-39 | OCH$_3$ | (methyl)-C(=N-O-NH-)-CH=C(2,4-(OCH$_3$)$_2$-C$_6$H$_3$) | Melting point: 139° C. |
| I-40 | OCH$_3$ | (methyl)-C(=N-O-N(CH$_3$)-)-CH=C(2,4-(OCH$_3$)$_2$-C$_6$H$_3$) | Oil |
| I-41 | OCH$_3$ | (methyl)-C(=N-N(CH$_3$)-)-C=CH-(2,4-(OCH$_3$)$_2$-C$_6$H$_3$) pyrazole | Oil |
| I-42 | OH | (methyl)-C(=N-O-)-CH=C(2,4-(OCH$_3$)$_2$-C$_6$H$_3$) | Melting point: 228° C. |
| I-43 | OH | (methyl)-C(=N-O-)-CH=C(4-CF$_3$-C$_6$H$_4$) | Melting point: 212° C. |
| I-44 | OH | (methyl)-C(=N-N(CH$_3$)-)-CH=C(2-CH$_3$-C$_6$H$_4$) | Melting point: 75° C. |
| I-45 | OH | (methyl)-C(=N-NH-)-CH=C(2,5-(CH$_3$)$_2$-C$_6$H$_3$) | Melting point: 195° C. |
| I-46 | OH | (methyl)-C(=N-N(CH$_3$)-)-CH=C(2,5-(CH$_3$)$_2$-C$_6$H$_3$) | Melting point: 73° C. |
| I-47 | OCH$_3$ | (methyl)-C(=N-N(COCH$_3$)-)-CH=C(C$_6$H$_5$) | Melting point: 121° C. |
| I-48 | OCH$_3$ | (methyl)-C(=N-N(C$_2$H$_5$)-)-CH=C(C$_6$H$_5$) | Melting point: 110° C. |
| I-49 | OH | (methyl)-C(=N-NH-)-CH=C(4-biphenyl) | Melting point: 236° C. |
| I-50 | OH | (methyl)-C(=N-N(CH$_3$)-)-CH=C(2,4-(OCH$_3$)$_2$-C$_6$H$_3$) | Melting point: 132° C. |

TABLE 1-continued

| Example No. | X | Het | Physical data |
|---|---|---|---|
| I-51 | OCH$_3$ | [2,4-dichlorophenyl group with N—N(CH$_3$) hydrazone] | Melting point: 109° C. |
| I-52 | OH | [4-chlorophenyl group with N—N(CH$_3$) hydrazone] | Melting point: 120° C. |
| I-53 | OCH$_3$ | [2,4-dichlorophenyl group with N—NH hydrazone] | Melting point: 171° C. |
| I-54 | OC$_2$H$_5$ | [4-methoxyphenyl group with N—N(C$_2$H$_5$) hydrazone] | Melting point: 90° C. |
| I-55 | OCH$_3$ | [phenyl group with N—N—C(O)CH$_2$OCH$_3$ hydrazone] | Oil |
| I-56 | OH | [tetrahydronaphthalene with N—N(CH$_3$) hydrazone] | Melting point: 118° C. |
| I-57 | OH | [tetrahydronaphthalene with N—NH hydrazone] | Melting point: 231° C. |
| I-58 | OCH$_3$ | [tetrahydronaphthalene with N—NH hydrazone] | Melting point: 64° C. |
| I-59 | OCH$_3$ | [tetrahydronaphthalene with N—N(CH$_3$) hydrazone] | Melting point: 140° C. |
| I-60 | OCH$_3$ | [cyclohexene with N—N(CH$_3$) hydrazone] | Melting point: 128° C. |
| I-61 | OCH$_3$ | [2,4-dichlorophenyl group with N—N(COCH$_3$) hydrazone] | |
| I-62 | OCH$_3$ | [2,4-dichlorophenyl group with CH$_3$C(O)N—N hydrazone] | |
| I-63 | OCH$_3$ | [cyclopentene with N—N(CH$_3$) hydrazone] | |
| I-64 | OCH$_3$ | [cyclopentene with N—N(CH$_3$) hydrazone] | |
| I-65 | OCH$_3$ | [cyclohexene with N(CH$_3$)—N hydrazone] | |

*with decomposition

The following starting substances of the general formula (II)

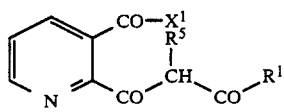 (II)

are obtained in accordance with Preparation Example (II-1) and under the process conditions stated above:

TABLE 2

| Example No. | $X^1$ | $R^1$ | $R^5$ | Physical data |
|---|---|---|---|---|
| II-2 | OCH₃ | —CH₂—CO—CH₃ | H | Oil |
| II-3 | OCH₃ | ⟨phenyl-OCH₃⟩ | | Melting point: 89° C. |
| II-4 | OCH₃ | —CH(CH₃)₂ | H | Oil |
| II-5 | OCH₃ | —C(CH₃)₃ | H | Oil |
| II-6 | OCH₃ | ⟨phenyl-Cl⟩ | H | Melting point: 99° C. |
| II-7 | OCH₃ | ⟨dichlorophenyl⟩ | H | Melting point: 85° C. |
| II-8 | OCH₃ | ⟨phenyl-CF₃⟩ | H | Melting point: 198–202° C. (decomposition) |
| II-9 | OCH₃ | ⟨naphthyl⟩ | H | Melting point: 106° C. |
| II-10 | OCH₃ | ⟨hydroxy-tetrahydronaphthyl⟩ | | Melting point: 91° C. |
| II-11 | OCH₃ | ⟨cyclohexanonyl⟩ | | Melting point: 74° C. |
| II-12 | OCH₃ | ⟨cyclopentanonyl⟩ | | Oil |

EXAMPLE A

Pre-emergence test/greenhouse
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and; after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

In this test the compound according to preparation Examples I-13 shows a very good herbicidal activity against monoctyledon and dicotyledon weeds.

EXAMPLE B

Post-emergence test/greenhouse
Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

In this test the compound according to preparation Example 13 shows a very good herbicidal activity against monoctyledon and dicotyledon weeds.

It is understood that the specification and examples are illustrative but not limitative of the present invention and that other embodiments within the spirit and scope of the invention will suggest themselves to those skilled in the art.

We claim:

1. A nicotinic acid derivative of the formula in which

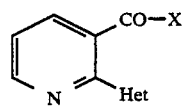

X represents hydroxy, or represents alkoxy with 1 to 6 carbon atoms, or represents the radical —OM, wherein
M represents a sodium or potassium ion, or represents one equivalent of a magnesium or calcium ion, or represents an ammonium or mono-, di-, tri- or tetraalkylammonium ion with in each case 1 to 4 carbon atoms in the individual alkyl radicals and
Het represents

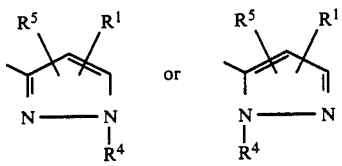

wherein
- R¹ represents straight-chain or branched alkyl with 1 to 6 carbon atoms, or represents alkenyl with 2 to 6 carbon atoms, or represents cycloalkyl with 3 to 6 carbon atoms, or represents acetyl, or represents phenyl or naphthyl, in each case optionally mono-, di- or trisubstituted by substituents independently selected from the group consisting of halogen, in each case straight-chain or branched alkyl, alkoxy, alkylthio and dialkylamino with 1 to 4 carbon atoms in the individual alkyl parts, halogenoalkyl with 1 or 2 carbon atoms and 1 to 5 identical or different halogen atoms, nitro and phenyl,
- R⁴ represents hydrogen, or represents straight-chain or branched alkyl with 1 to 6 carbon atoms, or represents optionally by fluorine, chlorine and/or bromine or $C_1$-$C_4$-alkoxy substituted $C_1$-$C_4$-alkyl-carbonyl, or represents phenyl which is optionally mono-, di- or trisubstituted by substituents independently selected from the group consisting of halogen, straight-chain or branched alkyl and alkoxy with in each case 1 to 4 carbon atoms and halogenoalky with 1 or 2 carbon atoms and 1 to 5 identical or different halogen atoms,
- R⁵ represents hydrogen.

2. A nicotinic acid derivative according to claim 1, in which
- X represents hydroxyl, methoxy, ethoxy or n- or i-propoxy, or represents the radical —OM, wherein
- M represents the sodium, potassium or ammonium ion or a tetraalkylammonium ion with 1 to 4 carbon atoms in the individual alkyl radicals, and
- Het represents

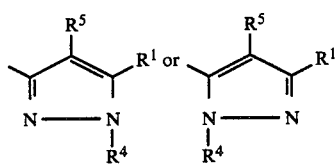

wherein
- R¹ represents methyl, ethyl, n- or i-propyl or n-, i-, s- or t-butyl, or represents cyclopropyl, cyclopentyl, cyclohexyl or acetyl, or represents phenyl or naphthyl, in each case optionally mono- or disubstituted by substituents independently selected from the group consisting of fluorine, chlorine, bromine, iodine, methyl, ethyl, n- and i-propyl, methoxy, ethoxy, n- and i-propoxy, methylthio, ethylthio, n- and i-propylthio, dimethylamino, diethylamino, dipropylamino, trifluoromethyl, nitro and phenyl, and
- R⁴ represents hydrogen, methyl, ethyl, n- or i-propyl, n-, i-, s- or t-butyl, acetyl, chloromethylcarbonyl, chloroethylcarbonyl, methoxymethylcarbonyl, ethoxymethylcarbonyl, methoxyethylcarbonyl, ethoxyethylcarbonyl,, or represents phenyl which is optionally mono- or disubstituted by substituents independently selected from the group consisting of fluorine, chlorine, bromine, methyl, ethyl, n- and i-propyl, methoxy, ethoxy, n- and i-propoxy and trifluoromethyl,
- R⁵ represents hydrogen.

3. A compound according to claim 1, wherein such compound is 2-(5-(4-methoxyphenyl)-1-methyl-pyrazol-3-yl)-3-carboxylic acid pyridine of the formula

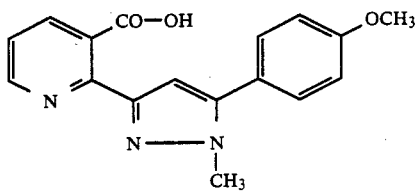

or an alkali metal, alkaline earth metal or ammonium salt thereof.

4. A compound according to claim 1, wherein such compound is 2-(1-methyl-5-phenyl-pyrazol-3-yl)-3-carboxylic acid pyridine of the formula

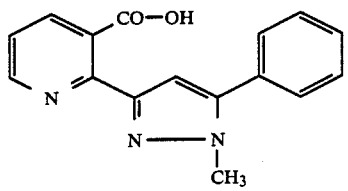

or an alkali metal, alkaline earth metal or ammonium salt thereof.

5. A compound according to claim 1, wherein such compound is 2-(5-(2,4-dichlorophenyl)-1-methyl-pyrazol-3-yl)-3-methoxycarbonyl-pyridine of the formula

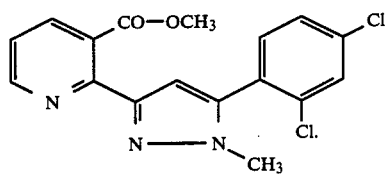

6. A compound according to claim 1, wherein such compound is 2-(5-(4-chlorophenyl)-1-methyl-pyrazol-3-yl)-3-carboxylic acid pyridine of the formula

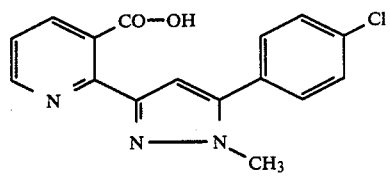

or an alkali metal, alkaline earth metal or ammonium salt thereof.

7. A herbicidal composition comprising a herbicidally effective amount of a compound according to claim 1 in admixture with a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is 2,(5-(2,4-dichlorophenyl)-1-methyl-pyrazol-3-yl)-3-methoxy-carbonyl-pyridine, or 2-(5-(4-methoxyphenyl)-1-methyl-pyrazol-3-yl)-3-carboxylic acid pyridine, 2-(1-methyl-5-phenyl-pyrazol-3-yl)-3-carboxylic acid pyridine or 2-(5-(4-chlorophenyl)-1-methyl-pyrazol-3-yl)-3-carboxylic acid pyridine, or an alkali metal, alkaline earth metal or ammonium salt thereof.

* * * * *